United States Patent
Niemi (12)

(10) Patent No.: US 6,340,412 B1
(45) Date of Patent: Jan. 22, 2002

(54) METHOD FOR DETERMINING THE DETACHING ANGLE AND/OR THE DETACHING PROFILE OF A PAPER WEB

(75) Inventor: Pertti Niemi, Vesanka (FI)

(73) Assignee: Fotocomp Oy, Jyvaskyla (FI)

( * ) Notice: Subject to any disclaimer, the term of this patent is extended or adjusted under 35 U.S.C. 154(b) by 0 days.

(21) Appl. No.: 09/674,406

(22) PCT Filed: Apr. 27, 1999

(86) PCT No.: PCT/FI99/00339

§ 371 Date: Oct. 26, 2000

§ 102(e) Date: Oct. 26, 2000

(87) PCT Pub. No.: WO99/60204

PCT Pub. Date: Nov. 25, 1999

(30) Foreign Application Priority Data

Apr. 27, 1998 (FI) .................................................. 980917
Dec. 17, 1998 (FI) .................................................. 982730

(51) Int. Cl.[7] ............................ D21F 7/00; G01N 33/34
(52) U.S. Cl. ............................... 162/198; 162/DIG. 11; 162/DIG. 10
(58) Field of Search ........................ 162/198, DIG. 10, 162/DIG. 11, 263, 202–204; 700/127–129; 348/88, 132, 188, 159; 382/108, 156–198

(56) References Cited

U.S. PATENT DOCUMENTS

| | | | | |
|---|---|---|---|---|
| 4,918,522 A | * | 4/1990 | Pajunen | 348/88 |
| 4,919,759 A | * | 4/1990 | Ilmarinen et al. | 162/206 |
| 4,955,720 A | * | 9/1990 | Blecha et al. | 356/429 |
| 4,991,007 A | * | 2/1991 | Corley | 348/188 |
| 5,011,573 A | * | 4/1991 | Niemi | 162/198 |
| 5,113,454 A | * | 5/1992 | Marcantonio et al. | 382/108 |
| 5,665,206 A | * | 9/1997 | Niskanen | 162/206 |
| 6,231,722 B1 | * | 5/2001 | Vestola | 162/198 |

FOREIGN PATENT DOCUMENTS

| | | | |
|---|---|---|---|
| WO | 94/12724 | * | 6/1994 |
| WO | 98/27275 | * | 6/1998 |

* cited by examiner

*Primary Examiner*—Jose Fortuna
(74) *Attorney, Agent, or Firm*—Fildes & Outland, P.C.

(57) ABSTRACT

A method for determining the detaching angle and/or detaching profile of a paper web wherein the paper web travels through sequential guide devices and detaches from a guide device so that the paper web deviates from a tangential angle from the detachment point onwards and the detachment point forms a detaching profile in the transverse direction of the paper web, which profile is determined with the aid of pattern recognition.

8 Claims, 1 Drawing Sheet

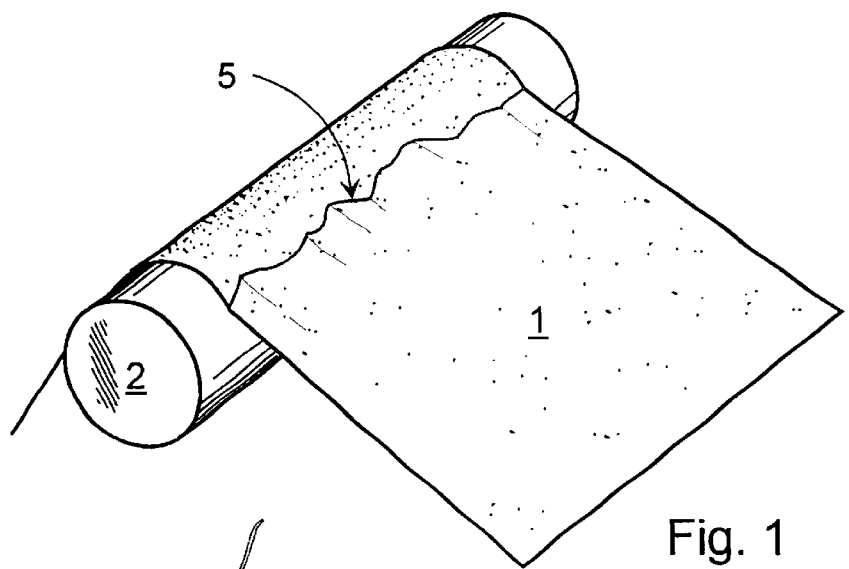
Fig. 1
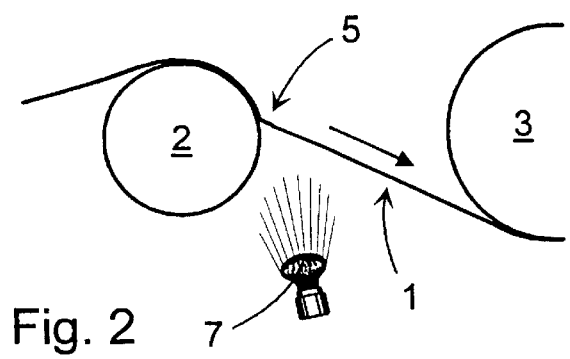
Fig. 2
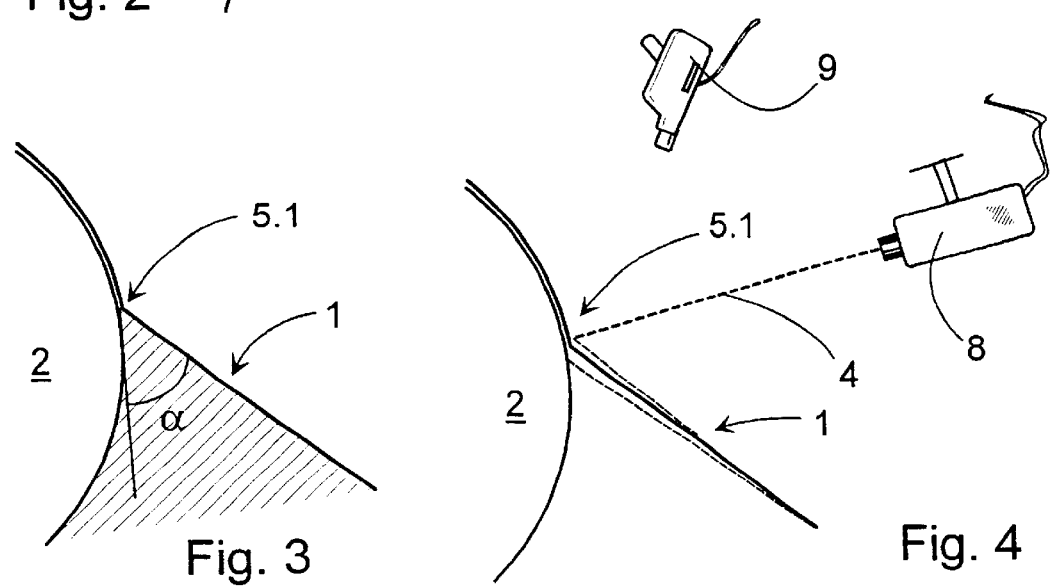
Fig. 3
Fig. 4

METHOD FOR DETERMINING THE DETACHING ANGLE AND/OR THE DETACHING PROFILE OF A PAPER WEB

TECHNICAL FIELD

The present invention relates to a method for determining the detaching angle and/or the detaching profile of a paper web, in which the paper web travels through sequential guide devices and detaches from a guide device, in such a way that the paper web deviates, from the detaching point onwards, from the tangential angle of the detaching point and that the detaching point forms a detaching profile in the transverse direction of the paper web.

BACKGROUND OF THE INVENTION

In conventional paper machines, there are some particular points, at which the paper web is detached from the surface of a guide device without support. Such a point is, for example, the removal of the web from the centre roll in the press section, when the web does not move tangentially to the next roll, but is sucked onto the centre roll, until there is sufficient gravity to deflect the web in the direction of the next roll. The point of detachment is determined by the properties of the web, in particular, its moisture content. In addition, dirt on the centre roll will affect the detachment of the paper from it. Detachment in the cross-machine direction does not take place exactly simultaneously, instead the detachment point forms a particular profile. This detaching profile correlates strongly with the moisture profile of the paper web, so that it can be exploited when determining the moisture profile. On the other hand, the aforesaid guide surface, for example, the dirtying of the roll, can greatly alter the detaching profile.

Previously, the detachment point has been measured using a laser scanner, which has determined the distance of the detachment point from a fixed point.

SUMMARY OF THE INVENTION

The present invention is intended to create a new kind of method for determining the detaching angle and/or detaching profile of a paper web. The addition of suitable lighting allows the detaching profile to be seen and thus to be recorded by video photography. Known pattern recognition devices can be used to define the boundary between the light and dark areas as a geometrical line.

According to one embodiment, the paper web is illuminated from below and photographed from above, when the through-lighting makes the detached paper web considerably lighter and the attached paper web appears as extremely dark.

According to another embodiment, the average location of the detachment point is illuminated with a laser photo-electric trip device and is photographed at an angle using a video camera, in which case the changes in the detachment point are clearly visible as movements of the image point in the video image.

In the following, the invention is described by reference to the accompanying illustrations, which show some embodiments according to the invention.

BRIEF DESCRIPTION OF THE DRAWINGS

FIG. 1 shows a paper web detaching from a roll, and forming a detaching profile on the roll surface.

FIG. 2 shows the detachment event seen from the side.

FIG. 3 shows the detachment event in detail.

FIG. 4 shows one other embodiment based on the use of a screen of laser light.

DETAILED DESCRIPTION OF THE INVENTION

In a paper machine, the paper web or track is guided by several different guide devices. These are rolls, cylinders, felts, wires, and other corresponding components. FIG. 1 shows the detachment event on the surface of the roll. The paper web arrives tangentially on roll 2, adheres weakly to the surface of the roll, which results in the paper web not detaching tangentially from the roll surface, but at some distance below the tangent. The detaching profile is drawn on FIG. 1, and is usually not quite straight, instead the detachment point varies when observed in the transverse direction, due to variations in the roll and the web. Usually, the detaching profile correlates directly with the moisture profile of the paper web, so that the moister points adhere more firmly to the surface of the roll and detach later from the roll surface than the drier points.

The detaching profile 5 is preferably depicted, for example, according to the arrangement in FIG. 2. Here, the paper web travels through guide roll 2 and detaches from it onto the next roll 3. The detaching profile can be photographed with a video camera 3 from above, at the same time as the paper web is illuminated from below, by means of light 7. The through-lit detaching paper web is clearly visible and, being considerably lighter, can be distinguished from the part of the web that remains on the surface of the roll. The video camera takes pictures at set intervals, from which it is easy to determine the boundary line between the dark and light areas by using a simple method. The pattern recognition of the boundary area is a quite simple operation.

It is preferable to determine the average detaching angle by photographing the detachment point at right-angles from the side and by lighting, for example, the upper surface, so that the lower surface remains in shadow. In that case, according to FIG. 3, the detachment point 5.1 appears as the point of a dark triangle, which separates the light end of the roll and the upper light areas. It is easy to use pattern recognition to determine the detaching angle α, the average detaching angle, the dispersion, and other statistical quantities.

The principles of pattern recognition and practical applications are described in the publication William K. Pratt, 'Digital Image Processing'; Wiley-Interscience Publications, John Wiley & Sons Inc.

FIG. 4 shows another embodiment, in which a screen of laser light 4 is used to illuminate the average detachment point at a nearly tangential angle. The light screen is formed by a laser transmitter 8, that is as such known, of which there are several in a row aimed at the same level. The camera 9 is set at an angle of 50° to the light screen 4. As a general instruction, the light screen 4 forms an angle of 75°–110° to the tangent and camera 9 is set at an angle of 30°–60° to the light screen 4. Thus, when the detachment point 5.1 varies transversely (shown by the broken line) the detachment point varies vertically in the image and forms a direct image of the detaching profile.

The measurement system includes lighting, a CCD camera, a digitization card, a computer, a printer, and a recognition and calculation program.

What is claimed is:

1. A method for determining the detaching angle and/or detaching profile of a paper web, in which the paper web travels through sequential first and second guide devices and detaches from the first guide device so that the paper web deviates from a tangential angle from the detachment point onwards and the detachment point forms a detachment profile in the transverse direction of the paper web, characterized in that the detaching profile is illuminated over the entire width of the paper web in such a way that an optically visible difference is created between the paper web that is attached to the first guide device and that which has detached from it, and the detaching profile is photographed from one side of the web using at least one video camera, and a value and/or group of values depicting the desired detachment profile is formed from the video image with the aid of pattern recognition.

2. A method according to claim 1, characterized in that the paper web is illuminated from one side and photographed from the other, so that the paper web that has detached from the first guide device is through-lit while the paper web attached to on the first guide device remains dark.

3. A method according to claim 2, characterized in that it also includes a video camera placed at right angles to the side of the average detachment point and a lighting system to emphasize the detaching angle in the video image and a pattern recognition system to determine the detaching angle.

4. A method according to claim 1, characterized in that the detaching profile of the paper web is photographed by means of two cameras, which are set on both sides of the paper web to photograph the detaching profile at an angle.

5. A method according to claim 4, characterized in that it also includes a video camera placed at right angles to the side of the average detachment point and a lighting system to emphasize the detaching angle in the video image and a pattern recognition system to determine the detaching angle.

6. A method according to claim 1, characterized in that a laser light screen is set to intersect the average location of the detaching profile being investigated, so that the laser light screen forms an angle of 75°–110° with a tangent at the average detachment point, and camera is set at an angle of 30°–60° with respect to the laser light screen.

7. A method according to claim 6, charcterized in that it also includes a video camera placed at right angles to the side of the average detachment point and a lighting system to emphasize the detaching angle in the video image and a pattern recognition system to determine the detaching angle.

8. A method according to claim 1, characterized in that it also includes a video camera placed at right angles to the side of the average detachment point and a lighting system to emphasize the detaching angle in the video image and a pattern recognition system to determine the detaching angle.

* * * * *